| United States Patent [19] | [11] | 4,118,569 |
|---|---|---|
| Berkowitz | [45] | Oct. 3, 1978 |

[54] CHLOROISOCYANURATE COMPOUNDS

[75] Inventor: Sidney Berkowitz, Highland Park, N.J.

[73] Assignee: FMC Corporation, Philadelphia, Pa.

[21] Appl. No.: 706,275

[22] Filed: Jul. 19, 1976

[51] Int. Cl.$^2$ .......................................... C07D 251/36
[52] U.S. Cl. .................................................... 544/190
[58] Field of Search ..................... 260/248 C; 544/190

[56] References Cited

U.S. PATENT DOCUMENTS

| 3,035,057 | 5/1962 | Symes et al. | 260/248 C |
| 3,072,654 | 1/1963 | Vazopolos | 260/248 C |
| 3,150,132 | 9/1964 | Symes | 260/248 C |
| 3,221,014 | 11/1965 | Symes | 260/248 C |
| 3,256,199 | 6/1966 | Symes | 252/99 |
| 3,272,813 | 9/1966 | Symes | 260/248 |
| 3,275,630 | 9/1966 | Symes | 260/248 |
| 3,325,411 | 6/1967 | Stepanek | 252/99 |
| 3,501,468 | 3/1970 | Moore et al. | 260/248 |
| 3,538,005 | 11/1970 | Weinstein et al. | 252/99 |
| 3,888,856 | 6/1975 | Wojtowicz | 260/248 C |
| 3,894,017 | 7/1975 | Wojtowicz | 260/248 C |
| 3,898,223 | 8/1975 | Wojtowicz | 260/248 C |

*Primary Examiner*—John M. Ford
*Attorney, Agent, or Firm*—Christine M. Miles; Frank Ianno

[57] ABSTRACT

Novel hydrated, potassium-containing chloroisocyanurate complex compounds and mixtures thereof are described together with processes for preparing the same. The novel compounds of this invention, namely, [(mono-trichloro,) tetra-(monopotassium dichloro,)] penta-isocyanurate tetrahydrate, and hydrated (mono-trichloro,) (monopotassium dichloro,) di-isocyanurate and mixtures thereof, are prepared by reacting in a substantially dry state trichloroisocyanuric acid and potassium dichloroisocyanurate monohydrate, the reaction products being determined by the molecular ratio of the starting materials. These novel compounds are resistant to burning, will not undergo self-propagating decomposition when subjected to a source of intense heat, as for example a hot wire, and are useful as a source of available chlorine in, for example bleaching, sterilizing, oxidizing and disinfecting operations. Further, the novel compounds of this invention and mixtures thereof can be dehydrated to produce the corresponding non-hydrated compounds, namely [(mono-trichloro,) tetra-(monopotassium dichloro,)] penta-isocyanurate and (mono-trichloro,) (monopotassium dichloro,) di-isocyanurate and mixtures thereof, which non-hydrated compounds and mixtures thereof are known in the art and are useful as a source of available chlorine.

14 Claims, No Drawings

CHLOROISOCYANURATE COMPOUNDS

This invention relates to novel hydrated potassium-containing chloroisocyanurate complex compounds, to mixtures thereof, and to processes for preparing such novel compounds and mixtures thereof. The invention further relates to processes for converting these novel compounds into certain known non-hydrated compounds, namely [(mono-trichloro,) tetra-(monopotassium dichloro,)] penta-isocyanurate and (mono-trichloro,) (monopotassium dichloro,) di-isocyanurate and mixtures thereof.

Dichloroisocyanuric acid, trichloroisocyanuric acid, alkali metal salts of dichloroisocyanuric acid and hydrates of said alkali metal salts are well known as sources of available chlorine and are useful, for example, in bleaching, sterilizing, oxidizing and disinfecting operations. Other known sources of available chlorine include two non-hydrated chloroisocyanurate complex compounds, namely [(mono-trichloro,) tetra-(monopotassium dichloro,)] penta-isocyanurate and (mono-trichloro,) (monopotassium dichloro,) di-isocyanurate, referred to as Compound I and Compound II respectively. Compounds I and II, and processes for their preparation are disclosed in U.S. Pat. Nos. 3,150,132, 3,272,813 (Division of 3,150,132), 3,275,630 (Continuation-in-part of 3,150,132), and 3,501,468.

The above mentioned patents disclose one process for the exclusive preparation of Compound I, and processes for the preparation of either Compounds I or II singly, or mixtures thereof. All of the disclosed processes involve liquid state reactions in aqueous solvent systems which require careful control of pH and reactant ratios.

Specifically, U.S. Pat. No. 3,275,630 discloses the exclusive preparation of Compound I by reacting an aqueous solution of monopotassium dichloroisocyanurate with an acid incapable of undergoing an oxidation-reduction reaction with the chloroisocyanurate starting material and reaction product. The acid reactant must be added to the reaction zone in an amount and at a rate sufficient to maintain a pH within the range 4.6–5.0.

U.S. Pat. No. 3,150,132 discloses a process for the preparation of either Compounds I or II singly, or mixtures thereof, by reacting chlorine and an aqueous solution of tripotassium cyanurate in a reaction zone containing a heel of an aqueous slurry of Compounds I or II or a mixture thereof. The particular compound or mixture produced depends upon the pH of the reaction system which is adjusted by controlling the rate of introducing the chlorine and tripotassium cyanurate into the reaction zone. U.S. Pat. No. 3,501,468 discloses a variation of this process which involves substitution of the tripotassium cyanurate reactant with a specifically defined sodium-potassium cyanurate compound.

Lastly, U.S. Pat. Nos. 3,150,132 and 3,272,813 disclose a process for the preparation of either Compounds I or II singly, or mixtures thereof, by reacting monopotassium dichloroisocyanurate and trichloroisocyanuric acid in an inert liquid. The particular compound or mixture produced depends upon the pH of the inert liquid and the ratio of reactants which are accordingly adjusted and controlled.

There are serious disadvantages to the prior art processes for the production of Compounds I and II. Firstly, the careful control of pH and reactant ratios required is difficult to achieve, especially where large scale commercial production is involved. Secondly, chlorinated isocyanurates, particularly trichloroisocyanuric acid, decompose in aqueous solvent systems to produce nitrogen trichloride, an extremely unstable compound which is explosive upon reaction with an organic compound, or at a temperature higher than 60° C. Decomposition of chlorinated cyanurates to form nitrogen trichloride is known to be pH dependent. Specifically, the decomposition of trichloroisocyanurate in aqueous solvent systems, to form nitrogen trichloride, peaks at a pH of about 5, which is near the midpoint of the pH range for formation of Compound I by the processes of the prior art (see U.S. Pat. No. 3,534,033). Consequently, there is a need for providing a process for production of Compounds I and II and mixtures thereof which has the practical advantage of not requiring careful pH control and the safety advantage of not producing dangerous levels of nitrogen trichloride.

With respect to active chlorine compounds per se, it is well known that many of such compounds, including certain anhydrous salts of chlorinated isocyanurates, burn when contacted with a flame and undergo self-propagating decomposition when subjected to a source of intense heat, as for example, a hot wire. The above present serious storage and handling problems. Consequently, there is a need for active chlorine compounds which are resistant to burning and to heat-induced self-propagating decomposition and therefore which can be safely and economically handled and stored.

It has been unexpectedly discovered that a novel crystalline potassium-containing chloroisocyanurate complex compound selected from the group consisting of [(mono-trichloro,) tetra-(monopotassium dichloro,)] penta-isocyanurate tetrahydrate, hydrated (mono-trichloro,) (monopotassium dichloro,) di-isocyanurate, said di-isocyanurate having from about 0.1 to about 1.0 moles of water of hydration, and mixtures thereof can be prepared by a process which comprises: bringing together and reacting in a substantially dry state, trichloroisocyanuric acid and potassium dichloroisocyanurate monohydrate in amounts such that the molar ratio of said acid to said monohydrate is in the range of 1:0.5 to 1:5.0. It has further been discovered that the product of the above described reaction of said acid and said monohydrate can be dried to produce a product having from about zero to about 0.2% by weight of water, the dried product being a compound selected from the group consisting of [(mono-trichloro,) tetra-(monopotassium dichloro,)] penta-isocyanurate, (mono-trichloro,) (monopotassium dichloro,) di-isocyanurate, and mixtures thereof.

It is one object of the present invention to provide novel hydrated crystalline potassium-containing chloro-isocyanurate complex compounds and mixtures thereof which have utility in bleaching, sanitizing and disinfecting operations, and which are resistant to burning and to heat-induced self-progagating decomposition.

It is another object of this invention to provide processes for preparing such novel compounds and mixtures thereof.

It is a further object of this invention to provide a process for preparing a non-hydrated crystalline potassium-containing chloroisocyanurate complex compound selected from the group consisting of [(mono-trichloro,) tetra-(monopotassium dichloro,)] penta-isocyanurate, (mono-trichloro,) (monopotassium dichloro,) di-isocyanurate, and mixtures thereof.

The present invention provides a novel hydrated potassium-containing chloroisocyanurate complex compound, namely, [(mono-trichloro,) tetra-(monopotassium dichloro,)] penta-isocyanurate tetrahydrate, having the general formula:

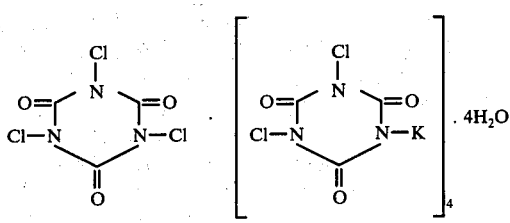

For convenience of description, this novel compound is referred to as Compound III.

Further, it will be understood throughout the specification and claims that various chemical terms are used interchangeably. For example, the terms "cyanurate" and "isocyanurate" refer to the same compounds but connotate different tautomeric forms thereof.

Compound III is a crystalline free-flowing solid, having a distinct X-ray diffraction pattern, and is further characterized in that it has an available chlorine content of about 62.5%, has about 5.7% by weight of water of hydration, and is soluble in distilled water at 25° C. to an extent of about 2.5% by weight. The pH of a 0.5% by weight aqueous solution thereof is about 4.33. Crystals of this compound exhibit a distinct elemental analysis which is described in Table I, immediately following the Examples.

The X-ray diffraction pattern of Compound III is unique and distinct from the X-ray diffraction patterns of trichloroisocyanuric acid, and potassium dichloroisocyanurate monohydrate. The X-ray diffraction pattern of said product is similar to, but different from, that of commercially available Compound I in that hydrate water peaks are observed, said peaks appearing at $2\theta$ values of 13.8 and 27.7. A typical X-ray diffraction pattern of Compound III is shown in Table II.

The differential thermal analysis curve of Compound III shows an endotherm at 65° C., verifying the presence of water of hydration.

Further, Compound III is non-burning when subjected to a horizontal flame propagation test and did not undergo self-propagating decomposition when subjected to a hot wire test. In addition, Compound III suppresses the burning rate of red oak sawdust. These thermal stability tests and the results thereof are discussed in detail in Examples V, VI and VII below.

Compound III will lose water of hydration on standing when exposed to air. Such loss, however, can be prevented by, for example, storage in sealed containers, or microencapsulation of the compound with materials such as modified dextrins, starches, and polyvinyl alcohols.

Compound III is prepared by bringing together and reacting in a substantially dry state, trichloroisocyanuric acid and potassium dichloroisocyanurate monohydrate in amounts such that the molar ratio of said acid to said monohydrate is in the range of 1:3.85 to 1:5.0. Preferably, the molar ratio of said acid to said monohydrate is in the range of 1:3.9 to 1:4.1.

Commercially available trichloroisocyanuric acid is entirely suitable for use in the process of this invention.

The potassium dichloroisocyanurate monohydrate reactant may be prepared by dissolving commercially available anhydrous potassium dichloroisocyanurate in water, filtering the solution to remove impurities, and cooling the filtrate to about 3° C. in a brine bath. The monohydrate crystals formed thereby are then filtered, washed with a suitable solvent as for example, acetone, and dried.

Preferably, the trichloroisocyanuric acid and potassium dichloroisocyanurate monohydrate are brought together and reacted by blending in, as for example, a tumble-type blender, a rotary tray apparatus or a ribbon blender. Although simple blending of a proper proportion of the reactants will produce Compound III, the reaction rate is greatly accelerated by compaction. Consequently, the most preferred method of reacting trichloroisocyanuric acid and potassium dichloroisocyanurate monohydrate to produce Compound III is to compact the blended product. Compaction pressures within the range of from about 1,000 psig to about 20,000 psig may be utilized. Formation of Compound III in quantitative yields is essentially complete upon compaction of the blended product.

Another novel cyanurate compound of this invention, namely, hydrated (mono-trichloro,) (monopotassium dichloro,) di-isocyanurate, has the general formula:

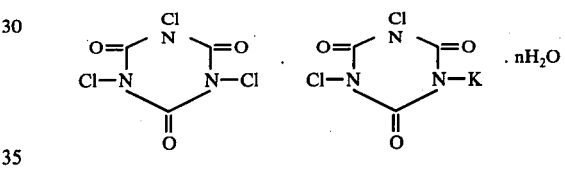

where $n$ is a number within the range of from about 0.1 to about 1.0. For convenience of description, this novel compound is referred to as Compound IV.

Compound IV, as prepared by the process of this invention, is not obtained in pure form. The various analyses set forth in Example III below suggest that the product obtained by the process of this invention contains Compound II together with Compound IV.

The X-ray diffraction pattern of said product containing Compound IV is unique and distinct from the X-ray diffraction pattern of Compound III, hereinbefore described, and is also distinct from the X-ray diffraction patterns of trichloroisocyanuric acid and potassium dichloroisocyanurate monohydrate. The X-ray diffraction pattern of said product is similar to, but different from, that of commercially available Compound II in that hydrate water peaks are observed, said peaks appearing at $2\theta$ values of 11.4 and 25.6. This X-ray diffraction data shows Compound IV to be a crystalline solid. A typical X-ray diffraction pattern of the product containing Compound IV is shown in Table IV.

The differential thermal analysis curve of the product containing Compound IV shows an endotherm at 69° C. from the water of hydration in Compound IV. Further, the product containing Compound IV does not undergo self-propagating decomposition when subjected to the hot wire test for thermal stability. This test and the results thereof are discussed in detail in Example VIII.

Compound IV will lose water of hydration on standing when exposed to air. Such loss, however, can be prevented by the same methods described above for Compound III.

Compound IV is prepared by bringing together and reacting in a substantially dry state, trichloroisocyanuric acid and potassium dichloroisocyanurate monohydrate in amounts such that the molar ratio of said acid to said monohydrate is in the range of 1:0.5 to 1:1.2. Preferably, the molar ratio of said acid to said monohydrate is in the range of 1:0.8 to 1:1.1.

The trichloroisocyanuric acid and potassium dichloroisocyanurate monohydrate are preferably brought together and reacted by blending. Although simple blending of a proper proportion of the reactants will produce Compound IV, the reaction is greatly accelerated by compaction. Consequently, the most preferred method of reacting trichloroisocyanuric acid and potassium dichloroisocyanurate monohydrate to produce Compound IV is to compact the blended product. Compaction pressures within the range of from about 1,000 psig to about 20,000 psig may be utilized.

Mixtures of Compounds III and IV may be prepared by altering the molecular ratio of the reactants in such a manner as to provide a molecular ratio of trichloroisocyanuric acid and potassium dichloroisocyanurate monohydrate in the range of from about 1:1.25 to about 1:3.8. Although simple blending of a proper proportion of the reactants will produce a mixture of Compounds III and IV, the reaction is greatly accelerated by compaction. Consequently, the most preferred method of reacting trichloroisocyanuric acid and potassium dichloroisocyanurate to produce a mixture of Compounds III and IV is to compact the blended product. Compaction pressures within the range of from about 1000 psig to about 20,000 psig may be utilized.

Further, it has been discovered that Compounds III and IV and mixtures thereof are relatively easily dehydrated to produce respectively either Compound I or II or mixtures thereof having from about zero to about 0.2% by weight of water. Any of the conventional means for removing water of hydration may be used, as for example, hot air drying, vacuum drying and fluidized bed drying. Compounds I and II are not prepared by blending and compacting stoichiometric amounts of anhydrous potassium dichloroisocyanurate and trichloroisocyanuric acid. X-ray diffraction patterns of such blended and compacted products show only a physical mixture of the reactants.

The above procedure results in a process for producing either Compounds I or II, singly, or mixtures thereof, wherein no special pH controls are required and no dangerous levels of nitrogen trichloride are produced. Specifically, either Compound I or II or mixtures thereof are produced by bringing together and reacting in a substantially dry state trichloroisocyanuric acid and potassium dichloroisocyanurate monohydrate in the proper molecular proportions, and drying the resultant product. As stated above, the reactants are preferably brought together and reacted by blending and compaction.

A further understanding of the products and processes of the present invention will be obtained from the following specific examples which are intended to illustrate this invention but not to limit the scope thereof.

EXAMPLE I

Preparation of [(mono-trichloro,) tetra-(monopotassium dichloro,)] penta-isocyanurate tetrahydrate, Compound III Commercially available trichloroisocyanuric acid was used in the reaction of this example. The potassium dichloroisocyanurate monohydrate reactant was prepared by dissolving 440 grams of commercially available potassium dichloroisocyanurate in 4,400 ml of water at a temperature within the range of 37° to 40° C. The solution was filtered to remove a small amount of insolubles, and the filtrate cooled to 3° C. in a brine bath. Well defined crystals of potassium dichloroisocyanurate monohydrate began forming at 12° C. The crystals were filtered, washed with 700 ml of acetone and air dried overnight.

Nine and twenty-eight hundredths grams (0.04 moles) of trichloroisocyanuric acid and 40.64 grams (0.16 moles) of potassium dichloroisocyanurate monohydrate were charged into a 500 ml tumble-type blender and blended for 15 minutes. 25 grams of the blended product were removed and compacted at a pressure of 12,000 psig in a hydraulic press. Pressure was maintained for 2 minutes. The compacted product was ground into a powder and subjected to the analysis described below.

Both compacted and non-compacted products were subjected to X-ray diffraction analyses. Additionally, the compacted product was analyzed for available chlorine by iodometric titration, and for water by a moisture balance operating at a temperature of about 160° C., and was subjected to elemental and differential thermal analyses.

The elemental analysis of the compacted product with respect to carbon, nitrogen, chlorine and potassium content, as shown in Table I, was in conformance with the amounts theoretically calculated for such elements from the hereinbefore referred to formula of Compound III.

The compacted product analyzed for 62.4% available chlorine (theory 62.64%) and for 5.7% water (theory 5.77%).

An endotherm at 65° C. in the differential thermal analysis curve of the compacted product verified the presence of water of hydration.

X-ray diffraction analyses of the non-compacted product showed formation of a small amount of Compound III immediately after blending the reactants, and formation of a major amount of Compound III 24 hours after said blending. The X-ray diffraction analysis of the compacted product performed immediately after compaction, showed formation of Compound III to be essentially complete. Obviously, compaction greatly accelerated the rate of reaction.

The X-ray diffraction pattern of Compound III is unique and distinct from the X-ray diffraction patterns of trichloroisocyanuric acid and potassium dichloroisocyanurate monohydrate. Further, the X-ray diffraction pattern of Compound III is similar to the pattern of commercially available Compound I except that hydrate water peaks are observed at 2θ values of 13.8 and 27.7. Table II shows the relative intensities, greater than 10%, of a typical X-ray diffraction pattern of Compound III.

Compound III was soluble in distilled water to the extent of about 2.5% by weight at a temperature of about 25° C., and a 0.5% solution thereof in distilled water had a pH of about 4.33.

EXAMPLE II

Run A — Example of the Inventions

Fifty grams of Compound III produced by the process of Example I, were heated in a vacuum oven at a temperature of 100° C. and under a pressure of 20 mm mercury for 1 hour, to produce Compound I. This dried product was analyzed for available chlorine by iodometric titration and for water by a moisture balance operating at a temperature of about 160° C., and was subjected to X-ray diffraction analysis.

The dried product analyzed for 66.2% available chlorine and for 0.02% water. Theoretical available chlorine and water values for Compound I are 66.3% and 0.0% respectively.

The X-ray diffraction pattern of the dried product was comparable to the pattern of commercially available Compound I.

Run B — Comparative Example

An attempt was made to prepare Compound I, by blending and then compacting commercially available samples of trichloroisocyanuric acid and anhydrous potassium dichloroisocyanurate at selected pressures.

In this test, 11.6 grams (0.05 moles) of trichloroisocyanuric acid and 47.2 grams (0.2 moles) of anhydrous potassium dichloroisocyanurate were charged into a 500 ml tumble-type blender and blended for 15 minutes.

The blended product was divided into three equal parts by weight, said parts being designated as Samples A, B and C. Each sample was compacted at a selected pressure in a hydraulic press. Specifically, Samples A, B and C were compacted at 10,000 psig, 15,000 psig and 20,000 psig respectively. The selected pressure was maintained for 2 minutes. Each compacted sample was ground into a powder, and subjected to X-ray diffraction analysis. The results of these analyses, set forth in Table III, showed that blending and compacting trichloroisocyanuric acid and potassium dichloroisocyanurate in a molecular ratio of about 1 to 4 respectively, formed no detectable amount of Compound I.

EXAMPLE III

Preparation of novel hydrated (mono-trichloro,) (monopotassium dichloro,) di-isocyanurate, or Compound IV Six and ninety-seven hundredths grams (0.03 moles) of commercially available trichloroisocyanuric acid and 7.62 grams (0.03 moles) of potassium dichloroisocyanurate monohydrate, prepared according to the procedure described in Example I, were charged into a 100 ml tumble-type blender and blended for 10 minutes.

Approximately 10 grams of the blended product were removed, and compacted at a pressure of 15,000 psig, using a hydraulic press. Pressure was maintained for 2 minutes. The compacted product was then ground into a powder. Both compacted and non-compacted products were subjected to X-ray diffraction analyses. Additionally, the compacted product was analyzed for available chlorine by iodometric titration, and for water by a moisture balance operating at a temperature of about 160° C. and was subjected to differential thermal analysis.

The compacted product analyzed for 72.92% available chlorine and 1.16% water. Theoretical values for available chlorine and water for pure Compound II are 72.86% and 3.70% respectively.

An endotherm at 69° C. in the differential thermal analysis curve of the compacted and ground product verifies the presence of water of hydration.

X-ray diffraction analyses showed formation of Compound IV, upon simple blending of the reactants. The rate of reaction, however, is greatly accelerated by compacting the blended product. Specifically, a relatively small product of Compound IV is formed in the blended product 24 hours after said blending, whereas a substantial amount of Compound IV is formed in the compacted product 24 hours after compaction.

The X-ray diffraction pattern of a typical blended and compacted product containing Compound IV is unique and distinct from the X-ray diffraction patterns of trichloroisocyanuric acid and potassium dichloroisocyanurate monohydrate. Further, the X-ray diffraction pattern of said product is similar to the pattern of commercially available Compound II except that hydrate water peaks are observed at $2\theta$ values of 11.4 and 25.6. This X-ray diffraction data, considered with the moisture analysis described above suggest that the product containing Compound IV also contains Compound II. Table IV shows the relative intensities, greater than 10%, of a typical X-ray diffraction pattern of the above described compacted product containing Compound IV.

EXAMPLE IV

Run A — Process of the Invention

Forty-eight and five tenths grams of product containing Compound IV, produced by the process of Example III, were heated in a vacuum oven at a temperature of 100° C. and under a pressure of 20 mm mercury for one hour, to produce Compound II. This dried product was analyzed for available chlorine by iodometric titration and for water by a moisture balance operating at a temperature of about 160° C., and was subjected to X-ray diffraction analysis.

The dried product analyzed for 75.3% available chlorine and for 0.05% water. Theoretical available chlorine and water values for Compound II are 75.8% and 0.0% respectively.

The X-ray diffraction pattern of the dried product was comparable to the pattern of commercially available Compound II.

Run B — Comparative Example

An attempt was made to prepare Compound II, by blending and then compacting commercially available samples of trichloroisocyanuric acid and anhydrous potassium dichloroisocyanurate at selected pressures.

Twenty-three and two tenths (0.1 moles) of trichloroisocyanuric acid and 23.6 grams (0.1 moles) of anhydrous potassium dichloroisocyanurate were charged into a 500 ml tumble-type blender, and blended for 15 minutes.

The blended product was divided into three equal parts by weight, said parts being designated as Samples D, E and F. Each sample was compacted at a selected pressure in a hydraulic press. Specifically, Samples D, E, and F were compacted at 10,000 psig, 15,000 psig and 20,000 psig respectively. The selected pressure was maintained for 2 minutes. Each compacted sample was ground into a powder, and subjected to X-ray diffraction analysis. The results of these analyses, set forth in Table V, show that blending and compacting trichloroisocyanuric acid and potassium dichloroisocyanurate in a molecular ratio of about 1 to 1, form no detectable amount of Compound II.

Examples V, VI and VII below compare the thermal stability of Compound III with the known corresponding anhydrous material, Compound I.

EXAMPLE V

An 18 gauge coiled nichrome wire was bent into a single 50 mm diameter loop and the ends of the wire were connected to a variable transformer. A 25 gram sample of Compound III produced by the process of Example I, was placed in a porcelain dish. The nichrome wire was inserted into the center of the mass, the variable transformer was activated, and the current was left on until the material in contact with the wire decomposed. The current was then turned off and the sample examined to determine the extent to which self-propagating decomposition occurred after the current was turned off.

The same procedure described above for Compound III was followed with a sample of commercially available Compound I.

Decomposition of Compound III ceased after the current was turned off. On the other hand, the decomposition of Compound I, initiated by the hot wire, self-propagated rapidly throughout the mass to give complete decomposition of the sample after the current was turned off.

EXAMPLE VI

Two samples, namely, Samples G and H were prepared, each containing 20% by weight of red oak sawdust. Sample G further contained 80% by weight of Compound III produced by the process of Example I, and Sample H further contained 80% by weight of commercially available Compound I. In addition, a control sample, Sample I, was prepared with red oak sawdust. The proposed Bureau of Mines Procedure RI 7594 was followed in preparing the samples and in performing the tests. Each sample was placed in a bed 1 × 2 × 7 inches and ignited with a flame. The burning rate was timed and the results set forth in Table VI show that Compound III suppresses the burning rate of red oak sawdust whereas Compound I, on the other hand, increases said burning rate.

EXAMPLE VII

Two hundred grams of Compound III, produced by the process of Example I and 200 grams of commercially available Compound I were individually place in a 1 × 2 × 7 inch bed and evaluated for horizontal flame propagation, following the procedure set forth in the Bureau of Mines Procedure RI 7593.

Compound III did not ignite, whereas Compound I, on the other hand, had a horizontal flame propagation rate of 1.1 inches per minute.

EXAMPLE VIII

A 25 gram sample of the product containing Compound IV, produced by the process of Example III, was subjected to the hot wire test described in Example V. Upon examining the sample after the current was turned off, no self-propagating decomposition occurred, that is, decomposition ceased after the current was turned off.

The invention being thus described, it will be obvious that the same may be varied in many ways. Such variations are not to be regarded as a departure from the spirit and scope of the invention, and all such modifications are intended to be included within the scope of the following claims.

TABLE I

Compound III: Elemental Analysis

| Element | Calculated Theoretical Percent | Found Percent |
| --- | --- | --- |
| Carbon | 14.41 | 14.67 |
| Nitrogen | 16.80 | 16.88 |
| Chlorine | 31.26 | 31.82 |
| Potassium | 12.52 | 13.65 |

TABLE II

Compound III: Typical X-Ray Diffraction Pattern (Data Includes Only Relative Intensities Greater than 10%)

| Angle 2 | Interplanar Spacing | Relative Intensity |
| --- | --- | --- |
| 13.8 | 6.41 | 22 |
| 22.0 | 4.03 | 19 |
| 22.5 | 3.95 | 36 |
| 25.0 | 3.55 | 16 |
| 27.3 | 3.26 | 100 |
| 28.6 | 3.11 | 70 |
| 29.5 | 3.02 | 11 |
| 33.9 | 2.64 | 30 |

TABLE III

X-ray Diffraction Analyses of Blended and Compacted Trichloroisocyanuric Acid and Anhydrous Potassium Dichloroisocyanurate (molecular ratio of 1 to 4 respectively)

| Sample | Compaction Pressure (psig) | X-ray Diffraction Analysis |
| --- | --- | --- |
| A | 10,000 | Intimate mixture of two components; no trace of complex formation |
| B | 15,000 | Intimate mixture of two components; no trace of complex formation |
| C | 20,000 | Intimate mixture of two components; no trace of complex formation |

TABLE IV

Compound IV: Typical X-ray Diffraction Pattern of a Compacted Product (Data includes only Relative Intensities Greater than 10%)

| Angle 2 | Interplanar Spacing | Relative Intensity |
| --- | --- | --- |
| 11.4 | 7.75 | 12 |
| 15.9 | 5.57 | 25 |
| 22.3 | 3.98 | 34 |
| 22.8 | 3.90 | 22 |
| 24.0 | 3.70 | 18 |
| 25.6 | 3.48 | 18 |
| 27.1 | 3.29 | 29 |
| 27.8 | 3.21 | 100 |
| 30.0 | 2.98 | 37 |
| 32.3 | 2.77 | 14 |
| 34.6 | 2.60 | 25 |
| 38.2 | 2.35 | 23 |

TABLE V

X-ray Diffraction Analyses of Blended and Compacted Trichloroisocyanuric Acid and Anhydrous Potassium Dichloroisocyanurate (molecular ratio of 1 to 1 respectively)

| Sample | Compaction Pressure (psig) | X-ray Diffraction Analysis |
| --- | --- | --- |
| D | 10,000 | Intimate mixture of two components; no trace of complex formation |
| E | 15,000 | Intimate mixture of two components; no trace of complex formation |
| F | 20,000 | Intimate mixture of two components; no trace of complex formation |

TABLE VI

Comparison of Burning Rates of Compounds I and III
Utilizing Proposed Bureau of Mines Procedure RI 7594

| Sample | Sample Composition | burning Rate in Minutes |
|---|---|---|
| G | 80% Compound III, 20% saw dust | 1.4 |
| H | 80% Compound I, 20% saw dust | 6.7 |
| I | 100% saw dust | 3.1 |

What is claimed is:

1. A process for preparing a crystalline, potassium-containing chloroisocyanurate complex compound selected from the group consisting of {(mono-trichloro,) tetra-(monopotassium dichloro,)} penta-isocyanurate tetrahydrate, hydrated (mono-trichloro,) (monopotassium dichloro,) di-isocyanurate, said di-isocyanurate having from about 0.1 to about 1.0 moles of water of hydration, and mixtures thereof, which comprises bringing together and reacting in a substantially dry state, trichloroisocyanuric acid and potassium dichloroisocyanurate monohydrate, in amounts such that the molar ratio of said acid to said monohydrate is in the range of 1:0.5 to 1:5.

2. Process of claim 1 wherein the trichloroisocyanuric acid and the potassium dichloroisocyanurate monohydrate are brought together and reacted by blending said acid and said monohydrate and then compacting the blended product under a pressure of from about 1000 psig to about 20,000 psig.

3. Process of claim 1 wherein the product of the reaction of said acid and said monohydrate is dried to produce a product having from about 0 to about 0.2% by weight of water.

4. A process for preparing {(mono-trichloro,) tetra-(monopotassium dichloro,)} penta-isocyanurate tetrahydrate which comprises bringing together and reacting in a substantially dry state, trichloroisocyanuric acid and potassium dichloroisocyanurate monohydrate, in amounts such that the molar ratio of said acid to said monohydrate is in the range of 1:3.85 to 1:5.0.

5. Process of claim 4 wherein the molar ratio of said acid to said monohydrate is in th range of 1:3.9 to 1:4.1.

6. Process of claim 4 wherein the trichloroisocyanuric acid and the potassium dichloroisocyanurate monohydrate are brought together and reacted by blending said acid and said monohydrate and then compacting the blended product under a pressure of about 1,000 psig to about 20,000 psig.

7. Process of claim 4 wherein the product of the reaction of said acid and said monohydrate is dried to produce a product having from about 0 to about 0.2% by weight of water.

8. A process for preparing hydrated (mono-trichloro,) (monopotassium dichloro,) di-isocyanurate, said di-isocyanurate having from about 0.1 mole to about 1.0 mole of water of hydration, which comprises bringing together and reacting in a substantially dry state, trichloroisocyanuric acid and potassium dichloroisocyanurate monohydrate, in amounts such that the molar ratio of said acid to said monohydrate is in the range of 1:0.5 to 1:1.2.

9. Process of claim 8 wherein the molar ratio of said acid to said monohydrate is in the range of 1:0.8 to 1:1.1.

10. Process of claim 8 wherein the trichloroisocyanuric acid and the potassium dichloroisocyanurate monohydrate are brought together and reacted by blending said acid and said monohydrate and then compacting the blending product under a pressure of from about 1,000 psig to about 20,000 psig.

11. Process of claim 8 wherein the product of the reaction of said acid and said monohydrate is dried to produce a product having from about 0 to about 0.2% by weight of water.

12. A process for preparing a mixture of {(mono-trichloro,) tetra-(monopotassium dichloro,) } penta-isocyanurate tetrahydrate and hydrated (mono-trichloro,) (monopotassium dichloro,) di-isocyanurate, said di-isocyanurate having from about 0.1 mole to about 1.0 mole of water of hydration, which comprises bringing together and reacting in a substantially dry state, trichloroisocyanuric acid and potassium dichloroisocyanurate monohydrate, in amounts such that the molar ratio of said acid to said monohydrate is in the range of 1:1.25 to 1:3.8.

13. Process of claim 12 wherein the trichloroisocyanuric acid and the potassium dichloroisocyanurate monohydrate are brought together and reacted by blending said acid and said monohydrate and then compacting the blending product under pressure of from about 1,000 psig to about 20,000 psig.

14. Process of claim 12 wherein the product of the reaction of said acid and said monohydrate is dried to produce a product having from about 0 to 0.2% by weight of water.

* * * * *